US010832871B2

(12) United States Patent
Petrzilek et al.

(10) Patent No.: US 10,832,871 B2
(45) Date of Patent: Nov. 10, 2020

(54) WET ELECTROLYTIC CAPACITOR FOR AN IMPLANTABLE MEDICAL DEVICE

(71) Applicant: AVX Corporation, Fountain Inn, SC (US)

(72) Inventors: Jan Petrzilek, Usti nad Orlici (CZ); Ilja Michalin, Trebic (CZ)

(73) Assignee: AVX Corporation, Fountain Inn, SC (US)

( * ) Notice: Subject to any disclaimer, the term of this patent is extended or adjusted under 35 U.S.C. 154(b) by 0 days.

(21) Appl. No.: 15/810,474

(22) Filed: Nov. 13, 2017

(65) Prior Publication Data

US 2018/0137989 A1 May 17, 2018

Related U.S. Application Data

(60) Provisional application No. 62/421,434, filed on Nov. 14, 2016.

(51) Int. Cl.
| | | |
|---|---|---|
| *H01G 9/145* | (2006.01) | |
| *H01G 9/00* | (2006.01) | |
| *A61N 1/39* | (2006.01) | |
| *H01G 9/035* | (2006.01) | |
| H01G 9/052 | (2006.01) | |

(52) U.S. Cl.
CPC .......... *H01G 9/145* (2013.01); *A61N 1/3981* (2013.01); *H01G 9/0029* (2013.01); *H01G 9/0032* (2013.01); *H01G 9/035* (2013.01); H01G 9/052 (2013.01)

(58) Field of Classification Search
None
See application file for complete search history.

(56) References Cited

U.S. PATENT DOCUMENTS

| | | | |
|---|---|---|---|
| 5,111,327 | A | 5/1992 | Blohm et al. |
| 5,329,428 | A | 7/1994 | Block et al. |
| 5,369,547 | A | 11/1994 | Evans |
| 5,457,862 | A | 10/1995 | Sakata et al. |
| 5,473,503 | A | 12/1995 | Sakata et al. |
| 5,716,511 | A | 2/1998 | Melody et al. |
| 5,812,367 | A | 9/1998 | Kudoh et al. |
| 6,162,345 | A | 12/2000 | Kinard et al. |

(Continued)

FOREIGN PATENT DOCUMENTS

| | | | |
|---|---|---|---|
| EP | 1 667 178 A1 | 6/2006 | |
| WO | WO2013186970 | * 1/2016 | ............... H01G 9/00 |

OTHER PUBLICATIONS

Machine Translation of WO2013/186970 (Year: 2016).*

(Continued)

*Primary Examiner* — Dion Ferguson
(74) *Attorney, Agent, or Firm* — Dority & Manning, P.A.

(57) ABSTRACT

A wet electrolytic capacitor that contains a cathode, fluidic working electrolyte, and anode that includes a sintered porous pellet is provided. A dielectric layer is also formed on a surface of the pellet and within its pores through anodic oxidation. The present inventors have discovered that through selective control over the anodic oxidation process, a substantially amorphous, low crystalline dielectric layer can be formed which, among other things, exhibits a leakage current that is smaller than previously thought possible for the high voltage capacitors employed in implantable medical devices.

19 Claims, 4 Drawing Sheets

(56) References Cited

U.S. PATENT DOCUMENTS

| | | |
|---|---|---|
| 6,197,252 B1 | 3/2001 | Bishop et al. |
| 6,231,993 B1 | 5/2001 | Stephenson et al. |
| 6,261,434 B1 | 7/2001 | Melody et al. |
| 6,267,861 B1 | 7/2001 | Kinard et al. |
| 6,346,185 B1 | 2/2002 | Kinard et al. |
| 6,430,026 B1 * | 8/2002 | Nagato ............... C25D 11/26 361/305 |
| 6,594,140 B1 | 7/2003 | Evans et al. |
| 6,635,729 B1 | 10/2003 | Groenendaal et al. |
| 6,674,635 B1 | 1/2004 | Fife et al. |
| 6,786,951 B2 | 9/2004 | He et al. |
| 6,987,663 B2 | 1/2006 | Merker et al. |
| 7,090,762 B2 | 8/2006 | Tripp et al. |
| 7,150,776 B2 | 12/2006 | Shekhter et al. |
| 7,169,284 B1 | 1/2007 | Jiang et al. |
| 7,248,462 B2 | 7/2007 | Melody et al. |
| 7,256,982 B2 | 8/2007 | Lessner et al. |
| 7,259,061 B2 | 8/2007 | Kundalgurki |
| 7,262,511 B2 | 8/2007 | Osako et al. |
| 7,483,260 B2 | 1/2009 | Ziarniak et al. |
| 7,515,396 B2 | 4/2009 | Biler |
| 7,544,218 B2 | 6/2009 | Norton et al. |
| 7,667,954 B2 | 2/2010 | Lessner et al. |
| 7,678,259 B2 | 3/2010 | Melody et al. |
| 7,727,372 B2 | 6/2010 | Liu et al. |
| 7,731,893 B2 | 6/2010 | Freeman et al. |
| 7,870,217 B2 | 2/2011 | Goad et al. |
| 7,952,853 B2 | 5/2011 | Viste et al. |
| 8,203,827 B2 | 6/2012 | Karnik |
| 8,313,538 B2 | 11/2012 | Merker et al. |
| 8,313,621 B2 | 11/2012 | Goad et al. |
| 8,477,479 B2 * | 7/2013 | Pease ................... H01G 9/008 29/25.03 |
| 8,675,348 B2 | 3/2014 | Viste et al. |
| 8,687,347 B2 | 4/2014 | Bates et al. |
| 9,053,854 B2 | 6/2015 | Petrzilek et al. |
| 9,105,401 B2 | 8/2015 | Dreissig et al. |
| 9,236,192 B2 | 1/2016 | Biler et al. |
| 9,384,901 B2 | 7/2016 | Weaver |
| 9,620,293 B2 | 4/2017 | Djebara et al. |
| 9,620,294 B2 | 4/2017 | Djebara et al. |
| 9,786,440 B2 | 10/2017 | Weaver et al. |
| 2003/0111247 A1 | 6/2003 | Araki et al. |
| 2004/0243183 A1 | 12/2004 | Norton et al. |
| 2008/0299371 A1 * | 12/2008 | Poltorak ............... H01G 9/052 428/220 |
| 2012/0176729 A1 * | 7/2012 | Pease ................... H01G 9/008 361/509 |
| 2016/0148757 A1 | 5/2016 | Djebara et al. |
| 2017/0263384 A1 * | 9/2017 | Naito ................... H01G 9/00 |
| 2018/0133493 A1 | 5/2018 | Petrzilek et al. |
| 2018/0137985 A1 | 5/2018 | Petrzilek et al. |

OTHER PUBLICATIONS

Pozdeev-Freeman et al., "Critical oxygen content in porous anodes of solid tantalum capacitors," *Journal of Materials Science: Materials in Electronics*, vol. 9, 1998, pp. 309-311.

International Search Report and Written Opinion PCT/US2017/061427 dated Feb. 6, 2018, 12 pages.

\* cited by examiner

WET ELECTROLYTIC CAPACITOR FOR AN IMPLANTABLE MEDICAL DEVICE

CROSS REFERENCE TO RELATED APPLICATION

The present application claims filing benefit of U.S. Provisional Patent Application Ser. No. 62/421,434 having a filing date of Nov. 14, 2016, and which is incorporated herein by reference in its entirety.

BACKGROUND OF THE INVENTION

High voltage electrolytic capacitors are often employed in implantable medical devices. These capacitors are required to have a high energy density because it is desirable to minimize the overall size of the implanted device. This is particularly true of an implantable cardioverter defibrillator ("ICD"), also referred to as an implantable defibrillator, because the high voltage capacitors used to deliver the defibrillation pulse can occupy as much as one third of the ICD volume. ICDs typically use two to four electrolytic capacitors in series to achieve the desired high voltage for shock delivery. Typically, metal foils (e.g., aluminum foil) are used in the electrolytic capacitor due to their small size. Because the electrostatic capacitance of the capacitor is proportional to its electrode area, the surface of the metallic foil may be, prior to the formation of the dielectric film, roughened or subjected to a chemical conversion to increase its effective area. This step of roughening the surface of the metallic foil is called etching. Etching is normally carried out either by the method (chemical etching) of conducting immersion into a solution of hydrochloric acid or by the method (electrochemical etching) of carrying out electrolysis in an aqueous solution of hydrochloric acid. The capacitance of the electrolytic capacitor is determined by the extent of roughing (the surface area) of the anode foil and the thickness and the dielectric constant of the oxide film.

Due to the limited surface area that may be provided by etching metallic foils, attempts have also been made to employ porous sintered pellets in wet electrolytic capacitors—i.e., "wet tantalum" capacitors. A tantalum pellet, for instance, may be formed by compressing a powder under high pressure and sintering at high temperature to form a sponge-like structure, which is very strong and dense but also highly porous. Unfortunately, however, it has traditionally been difficult to form dielectric layers on such pellets at the high voltages often required in ICD devices. For example, most formation processes require that a current is applied to the anodizing solution in a decreasing, stepwise fashion for a relatively long period of time (e.g., over 600 minutes) to achieve the desired voltage level. The present inventors have found, however, that overheating often occurs during such a process, which can lead to cracking in the dielectric and also result in a dramatic increase in the leakage current exhibited by the capacitor.

As such, a need currently exists for an improved wet electrolytic capacitor for use in implantable medical devices, such as defibrillators.

SUMMARY OF THE INVENTION

In accordance with one embodiment of the present invention, a wet electrolytic capacitor comprising an anode that comprises a pellet formed from a pressed and sintered valve metal powder. A dielectric layer is formed on the pellet that has no more than about 1,000 crystals per square millimeter or less. The capacitor also comprises a cathode that comprises a metal substrate coated with a conductive coating and a fluidic working electrolyte in communication with the anode and the cathode.

In accordance with another embodiment of the present invention, a method for forming a wet electrolytic capacitor is disclosed. The method comprises forming an anode by subjecting a sintered anode pellet to a formation profile, wherein the formation profile includes subjecting the pellet to an increasing current so that a target forming voltage is achieved in about 30 minutes or less, and positioning the anode and a fluidic working electrolyte within a casing.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of references characters in the present specification and drawings is intended to represent same or analogous features or elements of the invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

Generally speaking, the present invention is directed to a wet electrolytic capacitor that contains a cathode, fluidic working electrolyte, and anode that includes a sintered porous pellet. A dielectric layer is formed on a surface of the pellet and within its pores through anodic oxidation. The present inventors have discovered that through selective control over the anodic oxidation process, a substantially amorphous, low crystalline dielectric layer can be formed which, among other things, exhibits electrical properties (e.g., leakage current) better than previously thought possible for the high voltage capacitors employed in implantable medical devices. Namely, the dielectric typically has only about 1,000 crystals per square millimeter or less, in some embodiments about 500 crystals per square millimeter or less, and in some embodiments, from 0 to about 100 crystals per square millimeter.

Figure 5:
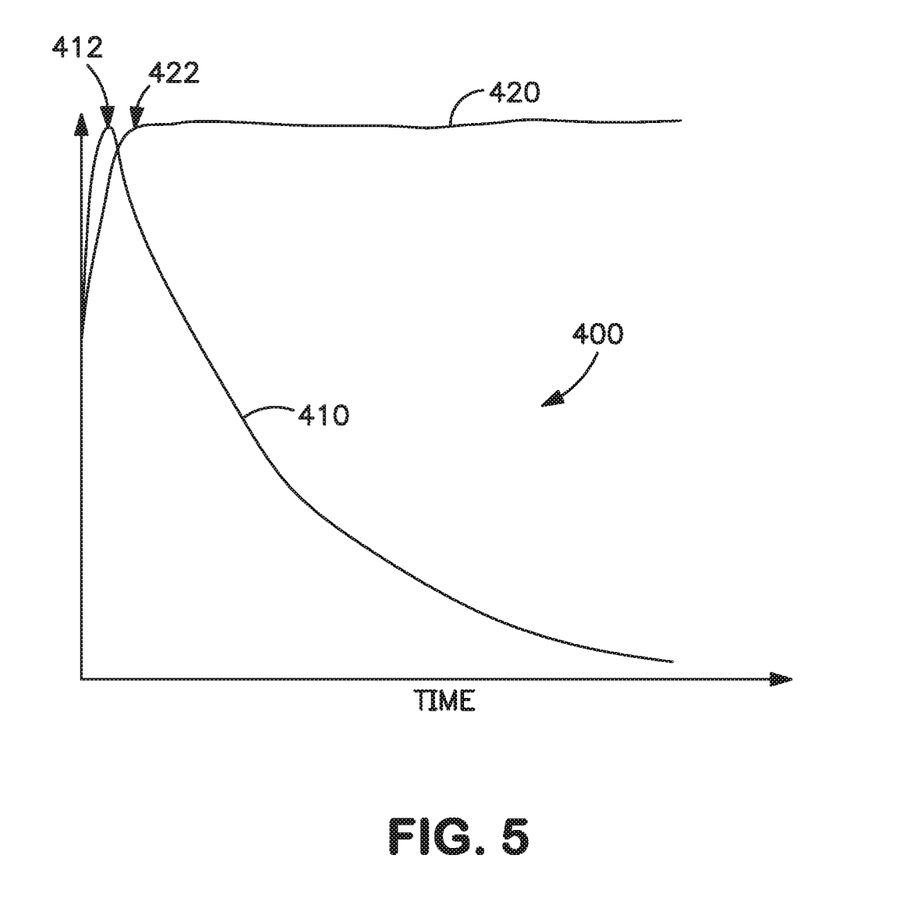
FIG. 5 is a graphical illustration of one embodiment of a formation profile that may be employed in the present invention.

While the exact mechanism is not fully understood, it is believed that such a low crystalline dielectric can be achieved by selectively controlling the formation profile so that the anode is subjected to a rapidly increasing current over a relatively short period of time until the target forming voltage (i.e., peak voltage) is achieved. Referring to FIG. 5, for example, one embodiment of a suitable formation profile 400 that may be employed in the present invention is shown. As illustrated, the formation profile 400 includes the application of a current 410 at a rapidly increasing rate until a peak current 412 is reached. The peak current 412 may, for instance, range from about 1000 to about 6000 milliamps, in some embodiments from about 1500 to about 5000 milliamps, and in some embodiments, from about 2500 to about 4000 milliamps. Notably, the peak current 412 can be reached in only a short period of time, such as about 30 minutes or less, in some embodiments about 20 minutes or less, and in some embodiments, from about 1 to about 15 minutes.

As the current 410 increases, the voltage 420 is also increased until a target forming voltage 422 is reached, which typically ranges from about 100 to about 500 volts, in some embodiments from about 150 to about 400 volts, and in some embodiments, from about 180 to about 300 volts. As with the peak current 412, the target forming voltage 422 is also reached in only a short period of time, such as about 30 minutes or less, in some embodiments about 20 minutes or less, and in some embodiments, from about 1 to about 15 minutes. After reaching the peak current value and target forming voltage, the current may then be reduced while the forming voltage is held at a relatively constant level to allow the thickness of the dielectric layer to continue to build. As shown in FIG. 5, for instance, the current 410 may be reduced at a non-linear rate (e.g., negative exponential rate) and/or the voltage 420 may be held relatively constant for a period of time ranging from about 20 minutes to about 300 minutes, in some embodiments from about 50 minutes to about 280 minutes, and in some embodiments, from about 100 minutes to about 250 minutes. In this manner, the total formation time is only typically from about 20 minutes to about 300 minutes, in some embodiments from about 50 minutes to about 280 minutes, and in some embodiments, from about 100 minutes to about 250 minutes.

Various embodiments of the present invention will now be described in more detail.

I. Anode

A. Pellet

The pellet is formed from a valve metal powder that contains a valve metal (i.e., metal that is capable of oxidation) or valve metal-based compound, such as tantalum, niobium, aluminum, hafnium, titanium, alloys thereof, oxides thereof, nitrides thereof, and so forth. For example, the valve metal powder may contain an electrically conductive oxide of niobium, such as niobium oxide having an atomic ratio of niobium to oxygen of 1:1.0±1.0, in some embodiments 1:1.0±0.3, in some embodiments 1:1.0±0.1, and in some embodiments, 1:1.0±0.05. The niobium oxide may be $NbO_{0.7}$, $NbO_{1.0}$, $NbO_{1.1}$, and $NbO_2$.

The powder may be formed using any of a variety of processes known in the art, such as electron beam melting, reduction, etc. A tantalum powder, for instance, may be formed by reducing a tantalum salt (e.g., potassium fluotantalate ($K_2TaF_7$), sodium fluotantalate ($Na_2TaF_7$), tantalum pentachloride ($TaCl_5$), etc.) with an alkali reducing agent (e.g., sodium).

In yet other embodiments, the powder may also be formed by reacting an oxide of a valve metal compound with a reducing agent that contains a metal having a relatively high oxidation state (e.g., magnesium). The valve metal oxide is typically a tantalum and/or niobium oxide capable of being reduced, such as $Ta_2O_x$ ($x \leq 5$) (e.g., $Ta_2O_5$) or $Nb_2O_x$ ($x \leq 5$) (e.g., $Nb_2O_5$). The reducing agent may be provided in a gaseous, liquid, or solid state, and may also be in the form of the metal, as well as alloys or salts thereof. In one embodiment, for instance, a halide salt (e.g., chloride, fluoride, etc.) may be employed. If desired, other components may also be added before, during, or after the reaction, such as dopants, alkali metals, etc. The reduction of the oxide is typically carried out at a temperature of from about 400° C. to about 1200° C., and in some embodiments, from about 600° C. to about 1000° C., for about 20 to about 300 minutes. Heating may be carried out in a reactor under an inert atmosphere (e.g., argon or nitrogen atmosphere) so that a molten bath is formed. Suitable reactors may include, for instance, vertical tube furnaces, rotary kilns, fluid bed furnaces, multiple hearth furnaces, self-propagation high-temperature synthesis reactors, etc. The reactor may be maintained under inert gas until that the mass in the reaction vessel is cooled to ambient temperature. Additional details of such a reduction reaction may be described in U.S. Patent Publication Nos. 2003/0110890 to He, et al. and 2004/0163491 to Shekhter, et al. After the reduction, the product may be cooled, crushed, and washed to remove excess impurities or reactants.

The resulting powder may be a free-flowing, finely divided powder that contains primary particles having any of a variety of shapes, such as a relatively flat shape (e.g., flakes) or three-dimensional shape (e.g., nodular or angular). When three-dimensional particles are employed, such particles typically have a relatively low "aspect ratio", which is the average diameter or width of the particles divided by the average thickness ("D/T"). For example, the aspect ratio of the particles may be about 4 or less, in some embodiments about 3 or less, and in some embodiments, from about 1 to about 2. The powder may also have a relatively high specific surface area, such as about 1 square meter per gram ("$m^2/g$") or more, in some embodiments about 2 $m^2/g$ or more, and in some embodiments, from about 4 to about 30 $m^2/g$. The term "specific surface area" generally refers to surface area as determined by the physical gas adsorption (B.E.T.) method of Bruanauer, Emmet, and Teller, Journal of American Chemical Society, Vol. 60, 1938, p. 309, with nitrogen as the adsorption gas. The test may be conducted with a MONO-SORB® Specific Surface Area Analyzer available from QUANTACHROME Corporation, Syosset, N.Y., which measures the quantity of adsorbate nitrogen gas adsorbed on a solid surface by sensing the change in thermal conductivity of a flowing mixture of adsorbate and inert carrier gas (e.g., helium).

The primary particles of the powder may also have a median size (D50) of from about 5 to about 250 nanometers, and in some embodiments, from about 10 to about 100 nanometers, such as using a laser particle size distribution analyzer made by BECKMAN COULTER Corporation (e.g., LS-230), optionally after subjecting the particles to an ultrasonic wave vibration of 70 seconds. Due to its high surface area and low particle size, the powder may have a high specific charge, such as greater than about 5,000 microFarads*Volts per gram ("µF*V/g"), in some embodiments from about 10,000 to about 80,000 µF*V/g, and in some embodiments, from about 15,000 to about 45,000 µF*V/g. As is known in the art, the specific charge may be determined by multiplying capacitance by the anodizing voltage employed, and then dividing this product by the weight of the anodized electrode body.

The powder (as well as the anode) may also have a relatively low alkali metal, carbon, and oxygen content. For example, the powder may have no more than about 50 ppm carbon or alkali metals, and in some embodiments, no more than about 10 ppm carbon or alkali metals. Likewise, the powder may have no more than about 0.15 ppm/μC/g oxygen, and in some embodiments, no more than about 0.10 ppm/μC/g oxygen. Oxygen content may be measured by LECO Oxygen Analyzer and includes oxygen in natural oxide on the tantalum surface and bulk oxygen in the tantalum particles. Bulk oxygen content is controlled by period of crystalline lattice of tantalum, which is increasing linearly with increasing oxygen content in tantalum until the solubility limit is achieved. This method was described in "Critical Oxygen Content In Porous Anodes Of Solid Tantalum Capacitors", Pozdeev-Freeman et al., Journal of Materials Science: Materials In Electronics 9, (1998) 309-311 wherein X-ray diffraction analysis (XRDA) was employed to measure period of crystalline lattice of tantalum. Oxygen in sintered tantalum anodes may be limited to thin natural surface oxide, while the bulk of tantalum is practically free of oxygen.

To facilitate the construction of the anode, certain additional components may also be included in the powder. For example, the powder may be optionally mixed with a binder and/or lubricant to ensure that the particles adequately adhere to each other when compacted or pressed to form the pellet. Suitable binders may include, for instance, poly(vinyl butyral); poly(vinyl acetate); poly(vinyl alcohol); poly(vinyl pyrollidone); cellulosic polymers, such as carboxymethyl-cellulose, methyl cellulose, ethyl cellulose, hydroxyethyl cellulose, and methylhydroxyethyl cellulose; atactic polypropylene, polyethylene; polyethylene glycol (e.g., Carbowax from Dow Chemical Co.); polystyrene, poly(butadiene/styrene); polyamides, polyimides, and polyacrylamides, high molecular weight polyethers; copolymers of ethylene oxide and propylene oxide; fluoropolymers, such as polytetrafluoroethylene, polyvinylidene fluoride, and fluoro-olefin copolymers; acrylic polymers, such as sodium polyacrylate, poly(lower alkyl acrylates), poly(lower alkyl methacrylates) and copolymers of lower alkyl acrylates and methacrylates; and fatty acids and waxes, such as stearic and other soapy fatty acids, vegetable wax, microwaxes (purified paraffins), etc. The binder may be dissolved and dispersed in a solvent. Exemplary solvents may include water, alcohols, and so forth. When utilized, the percentage of binders and/or lubricants may vary from about 0.1% to about 8% by weight of the total mass. It should be understood, however, that binders and/or lubricants are not necessarily required in the present invention.

The resulting powder may be compacted to form a pellet using any conventional powder press device. For example, a press mold may be employed that is a single station compaction press containing a die and one or multiple punches. Alternatively, anvil-type compaction press molds may be used that use only a die and single lower punch. Single station compaction press molds are available in several basic types, such as cam, toggle/knuckle and eccentric/crank presses with varying capabilities, such as single action, double action, floating die, movable platen, opposed ram, screw, impact, hot pressing, coining or sizing. The powder may be compacted around an anode lead wire. The wire may be formed from any electrically conductive material, such as tantalum, niobium, aluminum, hafnium, titanium, etc., as well as electrically conductive oxides and/or nitrides of thereof.

Any binder/lubricant may be removed after pressing by heating the pellet under vacuum at a certain temperature (e.g., from about 150° C. to about 500° C.) for several minutes. Alternatively, the binder/lubricant may also be removed by contacting the pellet with an aqueous solution, such as described in U.S. Pat. No. 6,197,252 to Bishop, et al.

Thereafter, the pellet is sintered to form a porous, integral mass. The pellet is typically sintered at a temperature of from about 800° C. to about 2000° C., in some embodiments from about 1200° C. to about 1800° C., and in some embodiments, from about 1500° C. to about 1700° C., for a time of from about 5 minutes to about 100 minutes, and in some embodiments, from about 8 minutes to about 15 minutes. This may occur in one or more steps. If desired, sintering may occur in an atmosphere that limits the transfer of oxygen atoms to the anode. For example, sintering may occur in a reducing atmosphere, such as in a vacuum, inert gas, hydrogen, etc. The reducing atmosphere may be at a pressure of from about 10 Torr to about 2000 Torr, in some embodiments from about 100 Torr to about 1000 Torr, and in some embodiments, from about 100 Torr to about 930 Torr. Mixtures of hydrogen and other gases (e.g., argon or nitrogen) may also be employed.

Upon sintering, the pellet shrinks due to the growth of metallurgical bonds between the particles. Because shrinkage generally increases the density of the pellet, lower press densities ("green") may be employed to still achieve the desired target density. For example, the target density of the pellet after sintering is typically from about 5 to about 8 grams per cubic centimeter. As a result of the shrinking phenomenon, however, the pellet need not be pressed to such high densities, but may instead be pressed to densities of less than about 6.0 grams per cubic centimeter, and in some embodiments, from about 4.5 to about 5.5 grams per cubic centimeter. Among other things, the ability to employ lower green densities may provide significant cost savings and increase processing efficiency.

Figure 2:
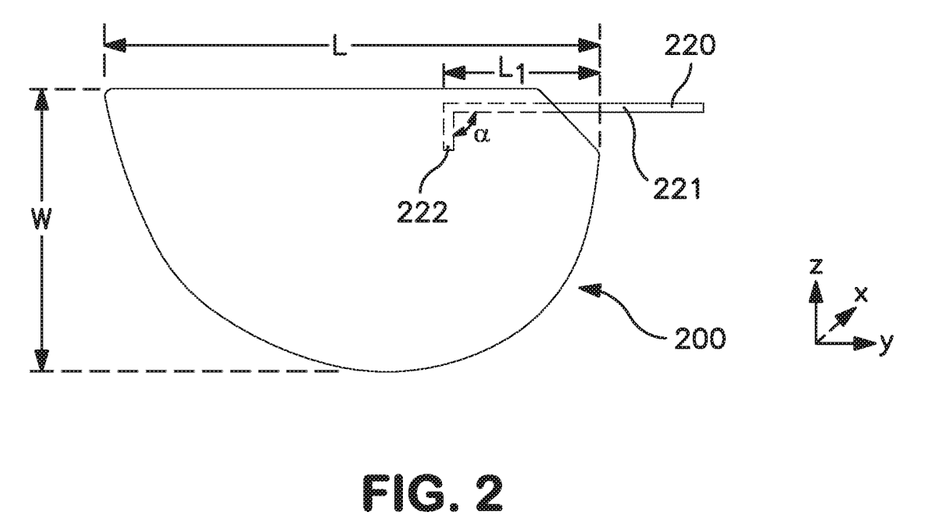
FIG. 2 is a top view of embodiment of an anode that may be employed in the capacitor of the present invention.
Figure 3:
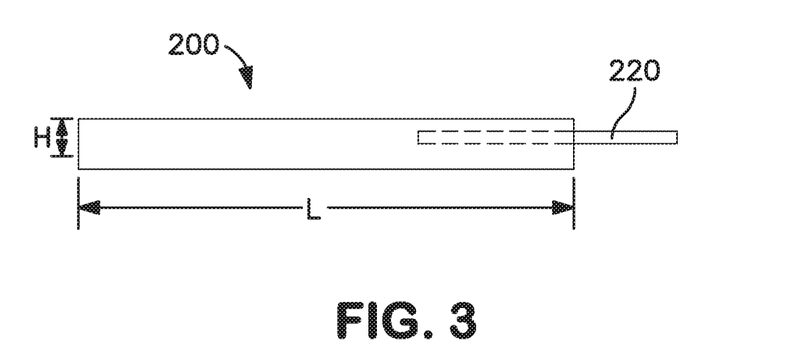
FIG. 3 is a frontal view of the anode of FIG. 2.

It is sometimes desirable to control the manner in which the anode wire is inserted to limit the extent that stresses applied during manufacturing will cause the wire to pull out of the anode. For example, in one embodiment, at least a portion of the wire within the anode is bent at an angle relative to the longitudinal axis of the wire. This "bend" reduces the ease to which the wire can be pulled out in the longitudinal direction after the anode is pressed and sintered. Referring to FIGS. 2-3, for example, one embodiment of a planar anode 200 is shown that contains an anode wire 220. The anode wire contains a first portion 221 that extends in a longitudinal direction ("y" direction) from the anode 200. Within the body of the anode, the wire 200 also contains a second portion 222 that is bent at an angle "a" relative to the first portion 221. The angle "a" is typically from about 40° to about 120°, in some embodiments from about 60° to about 110°, and in some embodiments, from about 80° to about 100° (e.g., about 90°). Such a bent configuration may be achieved in a variety of different ways. For example, in one embodiment, a press mold may be partially filled with the powder, and then a "pre-bent" anode wire may be inserted into the press mold. Thereafter, the mold may be filled with powder and the entire assembly compressed into a pellet.

In addition to its geometric configuration, the extent to which the anode wire is inserted into the anode may also be controlled to help minimize the likelihood of withdrawal during manufacturing. That is, the wire is less likely to be pulled out of the anode the farther it is inserted. Of course, too great of a wire insertion can alter the uniformity of the press density, which can impact the resulting electrical performance of the anode. In this regard, the present inventors have discovered that the ratio of the length of the anode in which the wire is inserted to the entire length of the anode is typically from about 0.1 to about 0.6, and in some embodiments, from about 0.2 to about 0.5. In FIG. 2, for example, the length "$L_1$" represents the length of the anode 200 in which the anode wire 220 is inserted, while the length "L" represents the entire length of the anode 200. In certain cases, the length "L" of the anode 200 may range from about 1 to about 80 millimeters, in some embodiments from about 10 to about 60 millimeters, and in some embodiments, from about 20 to about 50 millimeters. Likewise, the length "$L_1$" may be from about 1 to about 40 millimeters, in some embodiments, from about 2 to about 20 millimeters, and in some embodiments, from about 5 to about 15 millimeters. The width "W" of the anode may also be from about 0.05 to about 40 millimeters, in some embodiments, from about 0.5 to about 25 millimeters, and in some embodiments, from about 2 to about 10 millimeters.

The thickness of the anode is generally small to improve the electrical performance and volumetric efficiency of the resulting capacitor. In FIG. 3, for example, the thickness of a planar anode 200 is represented by the dimension "H." Typically, the thickness of the anode is about 5 millimeters or less, in some embodiments, from about 0.05 to about 4 millimeters, and in some embodiments, from about 0.1 to about 3.5 millimeters. The ratio of the length of the anode to the thickness of the anode is from about 5 to about 50, in some embodiments from about 6 to about 30, and in some embodiments, from about 7 to about 20. Although shown as a "D-shape" in FIG. 2, it should also be understood that the anode may possess any other desired shape, such as square, rectangle, circle, oval, triangle, etc. Polygonal shapes having more than four (4) edges (e.g., hexagon, octagon, heptagon, pentagon, etc.) are particularly desired due to their relatively high surface area.

B. Dielectric Layer

As indicated above, the anode also contains a dielectric layer formed by anodically oxidizing ("anodizing") the sintered anode pellet. For example, a tantalum (Ta) anode may be anodized to tantalum pentoxide ($Ta_2O_5$). Typically, anodization is performed by initially applying an electrolyte to the pellet, such as by dipping the pellet into the electrolyte. A current is thereafter passed through the electrolyte to form the dielectric layer in the manner described above. The temperature at which the anodic oxidation process is conducted may vary as desired, but is typically from about 10° C. to about 200° C., in some embodiments from about 20° C. to about 150° C., and in some embodiments, from about 25° C. to about 90° C.

The electrolyte is generally in the form of a liquid, such as a solution (e.g., aqueous or non-aqueous), dispersion, melt, etc. A solvent is generally employed in the electrolyte, such as water (e.g., deionized water); ethers (e.g., diethyl ether and tetrahydrofuran); alcohols (e.g., methanol, ethanol, n-propanol, isopropanol, and butanol); triglycerides; ketones (e.g., acetone, methyl ethyl ketone, and methyl isobutyl ketone); esters (e.g., ethyl acetate, butyl acetate, diethylene glycol ether acetate, and methoxypropyl acetate); amides (e.g., dimethylformamide, dimethylacetamide, dimethylcaprylic/capric fatty acid amide and N-alkylpyrrolidones); nitriles (e.g., acetonitrile, propionitrile, butyronitrile and benzonitrile); sulfoxides or sulfones (e.g., dimethyl sulfoxide (DMSO) and sulfolane); and so forth. The solvent may constitute from about 50 wt. % to about 99.9 wt. %, in some embodiments from about 75 wt. % to about 99 wt. %, and in some embodiments from about 80 wt. % to about 95 wt. % of the electrolyte. Although not necessarily required, the use of an aqueous solvent (e.g., water) is often desired to facilitate formation of an oxide. In fact, water may constitute about 1 wt. % or more, in some embodiments about 10 wt. % or more, in some embodiments about 50 wt. % or more, in some embodiments about 70 wt. % or more, and in some embodiments, about 90 wt. % to 100 wt. % of the solvent(s) used in the electrolyte.

The electrolyte is electrically conductive and may have an electrical conductivity of about 1 milliSiemens per centimeter ("mS/cm") or more, in some embodiments about 10 mS/cm or more, and in some embodiments, from about 20 mS/cm to about 100 mS/cm, determined at a temperature of 25° C. To enhance the electrical conductivity of the electrolyte, a compound may be employed that is capable of dissociating in the solvent to form ions. Suitable ionic compounds for this purpose may include, for instance, acids, such as hydrochloric acid, nitric acid, sulfuric acid, phosphoric acid, polyphosphoric acid, boric acid, boronic acid, etc.; organic acids, including carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid, citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; sulfonic acids, such as methanesulfonic acid, benzenesulfonic acid, toluenesulfonic acid, trifluoromethanesulfonic acid, styrenesulfonic acid, naphthalene disulfonic acid, hydroxybenzenesulfonic acid, dodecylsulfonic acid, dodecylbenzenesulfonic acid, etc.; polymeric acids, such as poly(acrylic) or poly(methacrylic) acid and copolymers thereof (e.g., maleic-acrylic, sulfonic-acrylic, and styrene-acrylic copolymers), carageenic acid, carboxymethyl cellulose, alginic acid, etc.; and so forth. The concentration of ionic compounds is selected to achieve the desired electrical conductivity. For example, an acid (e.g., phosphoric acid) may constitute from about 0.01 wt. % to about 5 wt. %, in some embodiments from about 0.05 wt. % to about 0.8 wt. %, and in some embodiments, from about 0.1 wt. % to about 0.5 wt. % of the electrolyte. If desired, blends of ionic compounds may also be employed in the electrolyte.

II. Working Electrolyte

The working electrolyte may be in electrical communication with the cathode and anode. The electrolyte is a fluid that may be impregnated within the anode, or it may be added to the capacitor at a later stage of production. The fluid electrolyte generally uniformly wets the dielectric on the anode. Various suitable electrolytes are described in U.S. Pat. Nos. 5,369,547 and 6,594,140 to Evans, et al. Typically, the electrolyte is ionically conductive in that has an electrical conductivity of from about 0.1 to about 20 Siemens per centimeter ("S/cm"), in some embodiments from about 0.2 to about 15 S/cm, and in some embodiments, from about 0.5 to about 10 S/cm, determined at a temperature of about 23° C. using any known electric conductivity meter (e.g., Oakton Con Series 11). The fluid electrolyte is generally in the form of a liquid, such as a solution (e.g., aqueous or non-aqueous), colloidal suspension, gel, etc. For example, the electrolyte may be an aqueous solution of an acid (e.g., sulfuric acid, phosphoric acid, or nitric acid), base (e.g., potassium hydroxide), or salt (e.g., ammonium salt, such as a nitrate), as well any other suitable electrolyte known in the art, such as a salt dissolved in an organic solvent (e.g., ammonium salt dissolved in a glycol-based solution). Various other electrolytes are described in U.S. Pat. Nos. 5,369, 547 and 6,594,140 to Evans, et al.

The desired ionic conductivity may be achieved by selecting ionic compound(s) (e.g., acids, bases, salts, and so forth) within certain concentration ranges. In one particular embodiment, salts of weak organic acids may be effective in achieving the desired conductivity of the electrolyte. The cation of the salt may include monatomic cations, such as alkali metals (e.g., $Li^+$, $Na^+$, $K^+$, $Rb^+$, or $Cs^+$), alkaline earth metals (e.g., $Be^{2+}$, $Mg^{2+}$, $Ca^{2+}$, $Sr^{2+}$ or $Ba^{2+}$), transition metals (e.g., $Ag^+$, $Fe^{2+}$, $Fe^{3+}$, etc.), as well as polyatomic cations, such as $NH_4^+$. The monovalent ammonium ($NH_4^+$), sodium ($K^+$), and lithium ($Li^+$) are particularly suitable cations for use in the present invention. The organic acid used to form the anion of the salt may be "weak" in the sense that it typically has a first acid dissociation constant ($pK_{a1}$) of about 0 to about 11, in some embodiments about 1 to about 10, and in some embodiments, from about 2 to about 10, determined at about 23° C. Any suitable weak organic acids may be used in the present invention, such as carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid (e.g., dextotartaric acid, mesotartaric acid, etc.), citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; blends thereof, and so forth. Polyprotic acids (e.g., diprotic, triprotic, etc.) are particularly desirable for use in forming the salt, such as adipic acid ($pK_{a1}$ of 4.43 and $pK_{a2}$ of 5.41), α-tartaric acid ($pK_{a1}$ of 2.98 and $pK_{a2}$ of 4.34), meso-tartaric acid ($pK_{a1}$ of 3.22 and $pK_{a2}$ of 4.82), oxalic acid ($pK_{a1}$ of 1.23 and $pK_{a2}$ of 4.19), lactic acid ($pK_{a1}$ of 3.13, $pK_{a2}$ of 4.76, and $pK_{a3}$ of 6.40), etc.

While the actual amounts may vary depending on the particular salt employed, its solubility in the solvent(s) used in the electrolyte, and the presence of other components, such weak organic acid salts are typically present in the electrolyte in an amount of from about 0.1 to about 25 wt. %, in some embodiments from about 0.2 to about 20 wt. %, in some embodiments from about 0.3 to about 15 wt. %, and in some embodiments, from about 0.5 to about 5 wt. %.

The electrolyte is typically aqueous in that it contains an aqueous solvent, such as water (e.g., deionized water). For example, water (e.g., deionized water) may constitute from about 20 wt. % to about 95 wt. %, in some embodiments from about 30 wt. % to about 90 wt. %, and in some embodiments, from about 40 wt. % to about 85 wt. % of the electrolyte. A secondary solvent may also be employed to form a solvent mixture. Suitable secondary solvents are described in more detail above. Such solvent mixtures typically contain water in an amount from about 40 wt. % to about 80 wt. %, in some embodiments from about 50 wt. % to about 75 wt. %, and in some embodiments, from about 55 wt. % to about 70 wt. % and secondary solvent(s) in an amount from about 20 wt. % to about 60 wt. %, in some embodiments from about 25 wt. % to about 50 wt. %, and in some embodiments, from about 30 wt. % to about 45 wt. %. The secondary solvent(s) may, for example, constitute from about 5 wt. % to about 45 wt. %, in some embodiments from about 10 wt. % to about 40 wt. %, and in some embodiments from about 15 wt. % to about 35 wt. % of the electrolyte.

If desired, the electrolyte may be relatively neutral and have a pH of from about 4.5 to about 8.0, in some embodiments from about 5.0 to about 7.5, and in some embodiments, from about 5.5 to about 7.0. One or more pH adjusters (e.g., acids, bases, etc.) may be employed to help achieve the desired pH. In one embodiment, an acid is employed to lower the pH to the desired range. Suitable acids include, for instance, organic acids such as described above; inorganic acids, such as hydrochloric acid, nitric acid, sulfuric acid, phosphoric acid, polyphosphoric acid, boric acid, boronic acid, etc.; and mixtures thereof. Although the total concentration of pH adjusters may vary, they are typically present in an amount of from about 0.01 wt. % to about 10 wt. %, in some embodiments from about 0.05 wt. % to about 5 wt. %, and in some embodiments, from about 0.1 wt. % to about 2 wt. % of the electrolyte.

The electrolyte may also contain other components that help improve the electrical performance of the capacitor. For instance, a depolarizer may be employed in the electrolyte to help inhibit the evolution of hydrogen gas at the cathode of the electrolytic capacitor, which could otherwise cause the capacitor to bulge and eventually fail. When employed, the depolarizer normally constitutes from about 1 to about 500 parts per million ("ppm"), in some embodiments from about 10 to about 200 ppm, and in some embodiments, from about 20 to about 150 ppm of the electrolyte. Suitable depolarizers may include nitroaromatic compounds, such as 2-nitrophenol, 3-nitrophenol, 4-nitrophenol, 2-nitrobenzonic acid, 3-nitrobenzonic acid, 4-nitrobenzonic acid, 2-nitroacetophenone, 3-nitroacetophenone, 4-nitroacetophenone, 2-nitroanisole, 3-nitroanisole, 4-nitroanisole, 2-nitrobenzaldehyde, 3-nitrobenzaldehyde, 4-nitrobenzaldehyde, 2-nitrobenzyl alcohol, 3-nitrobenzyl alcohol, 4-nitrobenzyl alcohol, 2-nitrophthalic acid, 3-nitrophthalic acid, 4-nitrophthalic acid, and so forth. Particularly suitable nitroaromatic depolarizers for use in the present invention are nitrobenzoic acids, anhydrides or salts thereof, substituted with one or more alkyl groups (e.g., methyl, ethyl, propyl, butyl, etc.). Specific examples of such alkyl-substituted nitrobenzoic compounds include, for instance, 2-methyl-3-nitrobenzoic acid; 2-methyl-6-nitrobenzoic acid; 3-methyl-2-nitrobenzoic acid; 3-methyl-4-nitrobenzoic acid; 3-methyl-6-nitrobenzoic acid; 4-methyl-3-nitrobenzoic acid; anhydrides or salts thereof; and so forth.

III. Cathode

A. Metal Substrate

The cathode typically contains a metal substrate, which may also optionally serve as a casing for the capacitor. The substrate may be formed from a variety of different metals, such as tantalum, niobium, aluminum, nickel, hafnium, titanium, copper, silver, steel (e.g., stainless), alloys thereof, composites thereof (e.g., metal coated with electrically conductive oxide), and so forth. The geometric configuration of the substrate may generally vary as is well known to those skilled in the art, such as in the form of a foil, sheet, screen, container, can, etc. The metal substrate may form the all or a portion of casing for the capacitor, or it may simply be applied to the casing. Regardless, the substrate may have a variety of shapes, such as generally cylindrical, D-shaped, rectangular, triangular, prismatic, etc. If desired, a surface of the substrate may be roughened to increase its surface area and increase the degree to which a material may be able to adhere thereto. In one embodiment, for example, a surface of the substrate is chemically etched, such as by applying a solution of a corrosive substance (e.g., hydrochloric acid) to the surface. Mechanical roughening may also be employed. For instance, a surface of the substrate may be abrasive blasted by propelling a stream of abrasive media (e.g., sand) against at least a portion of a surface thereof.

B. Conductive Coating

A conductive coating may also be disposed on a surface of the metal substrate (e.g., interior surface) to serve as an electrochemically active material for the capacitor. Any number of layers may be employed in the coating. The materials employed in the coating may vary. For example, the conductive coating may contain a noble metal (e.g., ruthenium, rhodium, palladium, silver, osmium, iridium, platinum, gold, etc.), an oxide (e.g., ruthenium oxide), carbonaceous materials, conductive polymers, etc. In one embodiment, for example, the coating may include conductive polymer(s) that are typically 7-conjugated and have electrical conductivity after oxidation or reduction. Examples of such π-conjugated conductive polymers include, for instance, polyheterocycles (e.g., polypyrroles, polythiophenes, polyanilines, etc.), polyacetylenes, poly-p-phenylenes, polyphenolates, and so forth. Substituted polythiophenes are particularly suitable for use as conductive polymer in that they have particularly good mechanical robustness and electrical performance. In one particular embodiment, the substituted polythiophene has the following general structure:

wherein,

T is O or S;

D is an optionally substituted $C_1$ to $C_5$ alkylene radical (e.g., methylene, ethylene, n-propylene, n-butylene, n-pentylene, etc.);

$R_7$ is a linear or branched, optionally substituted $C_1$ to $C_{18}$ alkyl radical (e.g., methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl, n-octadecyl, etc.); optionally substituted $C_5$ to $C_{12}$ cycloalkyl radical (e.g., cyclopentyl, cyclohexyl, cycloheptyl, cyclooctyl, cyclononyl cyclodecyl, etc.); optionally substituted $C_6$ to $C_{14}$ aryl radical (e.g., phenyl, naphthyl, etc.); optionally substituted $C_7$ to $C_{18}$ aralkyl radical (e.g., benzyl, o-, m-, p-tolyl, 2,3-, 2,4-, 2,5-, 2-6, 3-4-, 3,5-xylyl, mesityl, etc.); optionally substituted $C_1$ to $C_4$ hydroxyalkyl radical, or hydroxyl radical; and q is an integer from 0 to 8, in some embodiments, from 0 to 2, and in one embodiment, 0; and n is from 2 to 5,000, in some embodiments from 4 to 2,000, and in some embodiments, from 5 to 1,000. Example of substituents for the radicals "D" or "$R_7$" include, for instance, alkyl, cycloalkyl, aryl, aralkyl, alkoxy, halogen, ether, thioether, disulphide, sulfoxide, sulfone, sulfonate, amino, aldehyde, keto, carboxylic acid ester, carboxylic acid, carbonate, carboxylate, cyano, alkylsilane and alkoxysilane groups, carboxylamide groups, and so forth.

Particularly suitable thiophene polymers are those in which "D" is an optionally substituted $C_2$ to $C_3$ alkylene radical. For instance, the polymer may be optionally substituted poly(3,4-ethylenedioxythiophene), which has the following general structure:

Methods for forming conductive polymers, such as described above, are well known in the art. For instance, U.S. Pat. No. 6,987,663 to Merker, et al. describes various techniques for forming substituted polythiophenes from a monomeric precursor. The monomeric precursor may, for instance, have the following structure:

wherein,

T, D, $R_7$, and q are defined above. Particularly suitable thiophene monomers are those in which "D" is an optionally substituted $C_2$ to $C_3$ alkylene radical. For instance, optionally substituted 3,4-alkylenedioxythiophenes may be employed that have the general structure:

wherein, $R_7$ and q are as defined above. In one particular embodiment, "q" is 0. One commercially suitable example of 3,4-ethylenedioxthiophene is available from Heraeus Clevios under the designation Clevios™ M. Other suitable monomers are also described in U.S. Pat. No. 5,111,327 to Blohm, et al. and U.S. Pat. No. 6,635,729 to Groenendaal, et al. Derivatives of these monomers may also be employed that are, for example, dimers or trimers of the above monomers. Higher molecular derivatives, i.e., tetramers, pentamers, etc. of the monomers are suitable for use in the present invention. The derivatives may be made up of identical or different monomer units and used in pure form and in a mixture with one another and/or with the monomers. Oxidized or reduced forms of these precursors may also be employed.

The thiophene monomers may be chemically polymerized in the presence of an oxidative catalyst. The oxidative catalyst typically includes a transition metal cation, such as iron(III), copper(II), chromium(VI), cerium(IV), manganese (IV), manganese(VII), ruthenium(III) cations, etc. A dopant may also be employed to provide excess charge to the conductive polymer and stabilize the conductivity of the polymer. The dopant typically includes an inorganic or organic anion, such as an ion of a sulfonic acid. In certain embodiments, the oxidative catalyst employed in the precursor solution has both a catalytic and doping functionality in that it includes a cation (e.g., transition metal) and anion (e.g., sulfonic acid). For example, the oxidative catalyst may be a transition metal salt that includes iron(III) cations, such as iron(III) halides (e.g., $FeCl_3$) or iron(III) salts of other inorganic acids, such as $Fe(ClO_4)_3$ or $Fe_2(SO_4)_3$ and the iron(III) salts of organic acids and inorganic acids comprising organic radicals. Examples of iron (III) salts of inorganic acids with organic radicals include, for instance, iron(III) salts of sulfuric acid monoesters of $C_1$ to $C_{20}$ alkanols (e.g., iron(III) salt of lauryl sulfate). Likewise, examples of iron (III) salts of organic acids include, for instance, iron(III) salts of $C_1$ to $C_{20}$ alkane sulfonic acids (e.g., methane, ethane, propane, butane, or dodecane sulfonic acid); iron (III) salts of aliphatic perfluorosulfonic acids (e.g., trifluoromethane sulfonic acid, perfluorobutane sulfonic acid, or perfluorooctane sulfonic acid); iron (III) salts of aliphatic $C_1$ to $C_{20}$ carboxylic acids (e.g., 2-ethylhexylcarboxylic acid); iron (III) salts of aliphatic perfluorocarboxylic acids (e.g., trifluoroacetic acid or perfluorooctane acid); iron (III) salts of aromatic sulfonic acids optionally substituted by $C_1$ to $C_{20}$ alkyl groups (e.g., benzene sulfonic acid, o-toluene sulfonic acid, p-toluene sulfonic acid, or dodecylbenzene sulfonic acid); iron (III) salts of cycloalkane sulfonic acids (e.g., camphor sulfonic acid); and so forth. Mixtures of these above-mentioned iron(III) salts may also be used. Iron(III)-p-toluene sulfonate, iron(III)-o-toluene sulfonate, and mixtures thereof, are particularly suitable. One commercially suitable example of iron(III)-p-toluene sulfonate is available from Heraeus Clevios under the designation Clevios™ C.

Various methods may be utilized to form the conductive layer. In one embodiment, the oxidative catalyst and monomer are applied, either sequentially or together, such that the polymerization reaction occurs in situ on the substrate. Suitable application techniques may include screen-printing, dipping, electrophoretic coating, and spraying, may be used to form a conductive polymer coating. As an example, a monomer may initially be mixed with the oxidative catalyst to form a precursor solution. Once the mixture is formed, it may be applied to the metal substrate and then allowed to polymerize so that the conductive layer is formed. Alternatively, the oxidative catalyst and monomer may be applied sequentially. In one embodiment, for example, the oxidative catalyst is dissolved in an organic solvent (e.g., butanol) and then applied as a dipping solution. The substrate may then be dried to remove the solvent therefrom. Thereafter, the substrate may be dipped into a solution containing the monomer. Polymerization is typically performed at temperatures of from about −10° C. to about 250° C., and in some embodiments, from about 0° C. to about 200° C., depending on the oxidizing agent used and desired reaction time. Suitable polymerization techniques, such as described above, may be described in more detail in U.S. Publication No. 2008/232037 to Biler.

While chemical polymerization techniques may be employed in certain embodiments, it is often desired to minimize the use of oxidative catalysts in the capacitor as such materials can often lead to the formation of iron radicals (e.g., $Fe^{2+}$ or $Fe^{3+}$ ions). These radicals can, in turn, lead to dielectric degradation at the high voltages often employed during the use of the wet capacitor. Thus, anodic electrochemical polymerization techniques may be employed in certain embodiments to form the conductive polymer. Such techniques generally employ a colloidal suspension that is generally free of iron-based oxidative catalysts. For instance, the colloidal suspension typically contains less than about 0.5 wt. %, in some embodiments, less than about 0.1 wt. %, and in some embodiments, less than about 0.05 wt. % (e.g., 0 wt. %) of such iron-based oxidative catalysts.

The colloidal suspension may be in the form of a macroemulsion, microemulsion, solution, etc. depending on the particular nature of the components of the suspension. Regardless, the suspension generally contains a solvent that serves as a continuous phase within which the precursor monomer is dispersed. Any of a variety of different solvents may be employed in the colloidal suspension, such as alcohols, glycols, water, etc. In one particular embodiment, the colloidal suspension is aqueous in nature. If desired, other additives may also be employed in the suspension to facilitate polymerization, such as surfactants (e.g., nonionic, anionic, or cationic surfactants), dopants (e.g., sulfonic acids), defoaming agents, and so forth. Solvents (e.g., water) may constitute from about 50 wt. % to about 99 wt. %, in some embodiments from about 70 wt. % to about 98 wt. % and in some embodiments, from about 80 wt. % to about 95 wt. %. The remaining components of the colloidal suspension (e.g., precursor monomers, surfactants, and sulfonic acids) may likewise constitute from about 1 wt. % to about 50 wt. %, in some embodiments from about 2 wt. % to about 30 wt. % and in some embodiments, from about 5 wt. % to about 20 wt. % of the colloidal suspension.

To apply the colloidal suspension, any of a variety of suitable application techniques may be employed, such as screen-printing, dipping, electrophoretic coating, spraying, etc. Regardless of how it is applied, the monomer within the colloidal suspension may be anodically electrochemically-polymerized to form the conductive polymer layer. In one embodiment, for example, the metal substrate is dipped into a bath containing the colloidal suspension of the present invention. A pair of electrodes may be disposed within the bath for electrolysis. One electrode may be connected to the positive terminal of a power source and also in contact with the metal substrate. The other electrode may be connected to the negative terminal of the power source and an additional inert metal. During operation, the power source supplies a current feed to the electrodes in the electrochemical cell, thereby inducing electrolysis of the electrolyte and oxidative polymerization of the monomer in the colloidal suspension, or solution, onto the metal substrate. Anodic electrochemical polymerization is generally performed at ambient temperature to ensure that the colloidal suspension does not phase separate. For example, the colloidal suspension may be kept at a temperature of from about 15° C. to about 80° C., in some embodiments from about 20° C. to about 75° C., and in some embodiments, from about 25° C. to about 50° C. The amount of time in which the metal substrate is in contact with the colloidal suspension during anodic electrochemical polymerization may vary. For example, the metal substrate may be dipped into such a solution for a period of time ranging from about 10 seconds to about 10 minutes.

Multiple polymerization steps may be repeated until the desired thickness of the coating is achieved. In one embodiment, for example, a chemically polymerized layer may be formed directly over the noble metal layer and an electrochemical polymerized layer may be disposed thereover, or vice versa. Regardless, the total target thickness of the conductive polymer layer(s) may generally vary depending on the desired properties of the capacitor. Typically, the resulting conductive polymer layer(s) have a thickness of from about 0.2 micrometers ("µm") to about 50 µm, in some embodiments from about 0.5 µm to about 20 µm, and in some embodiments, from about 1 µm to about 5 µm. It should be understood that the thickness of the layers are not necessarily the same at all locations on the substrate. Nevertheless, the average thickness on the substrate generally falls within the ranges noted above.

Figure 1:
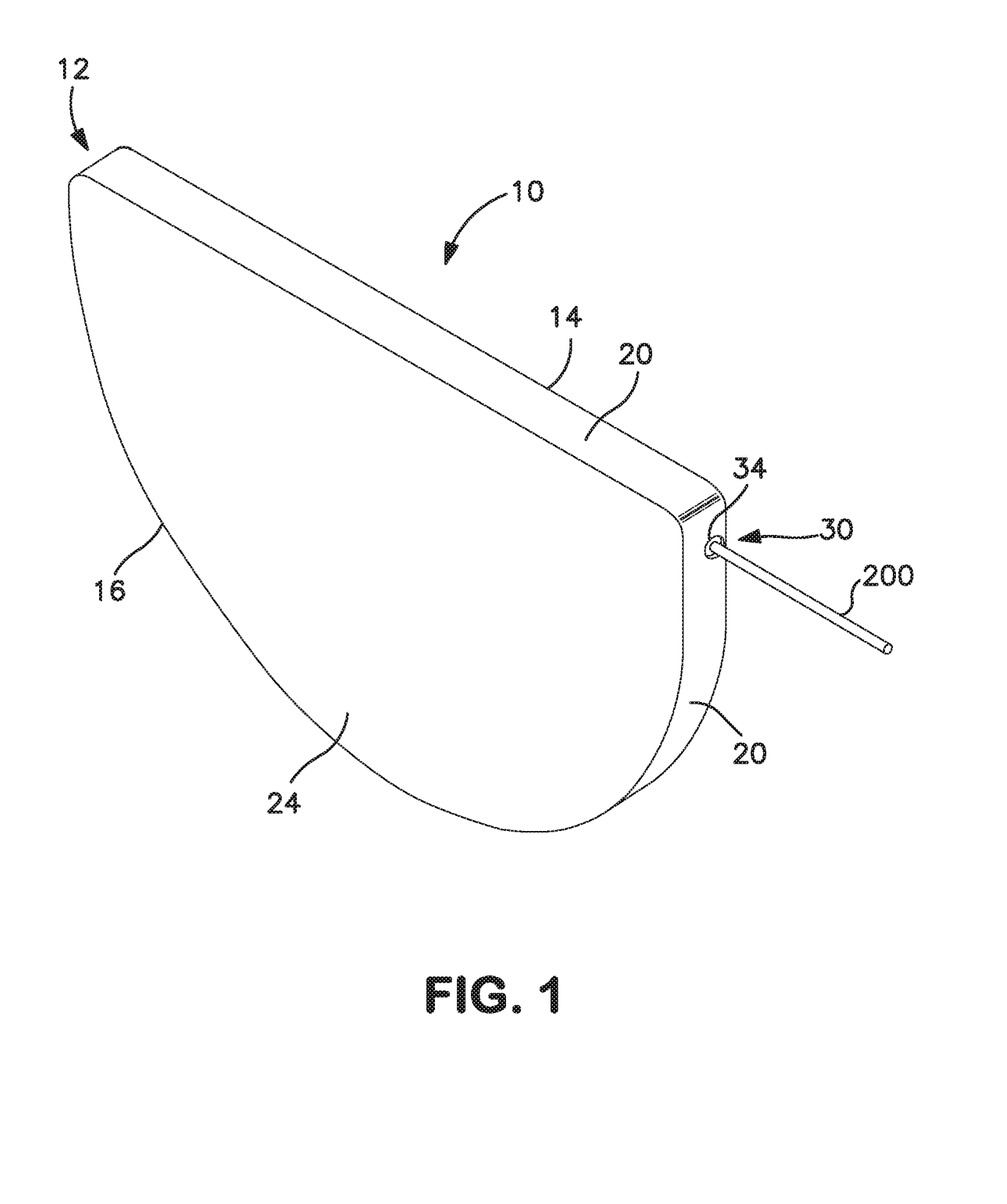
FIG. 1 is a perspective view of one embodiment of the wet electrolytic capacitor of the present invention.
Figure 4:
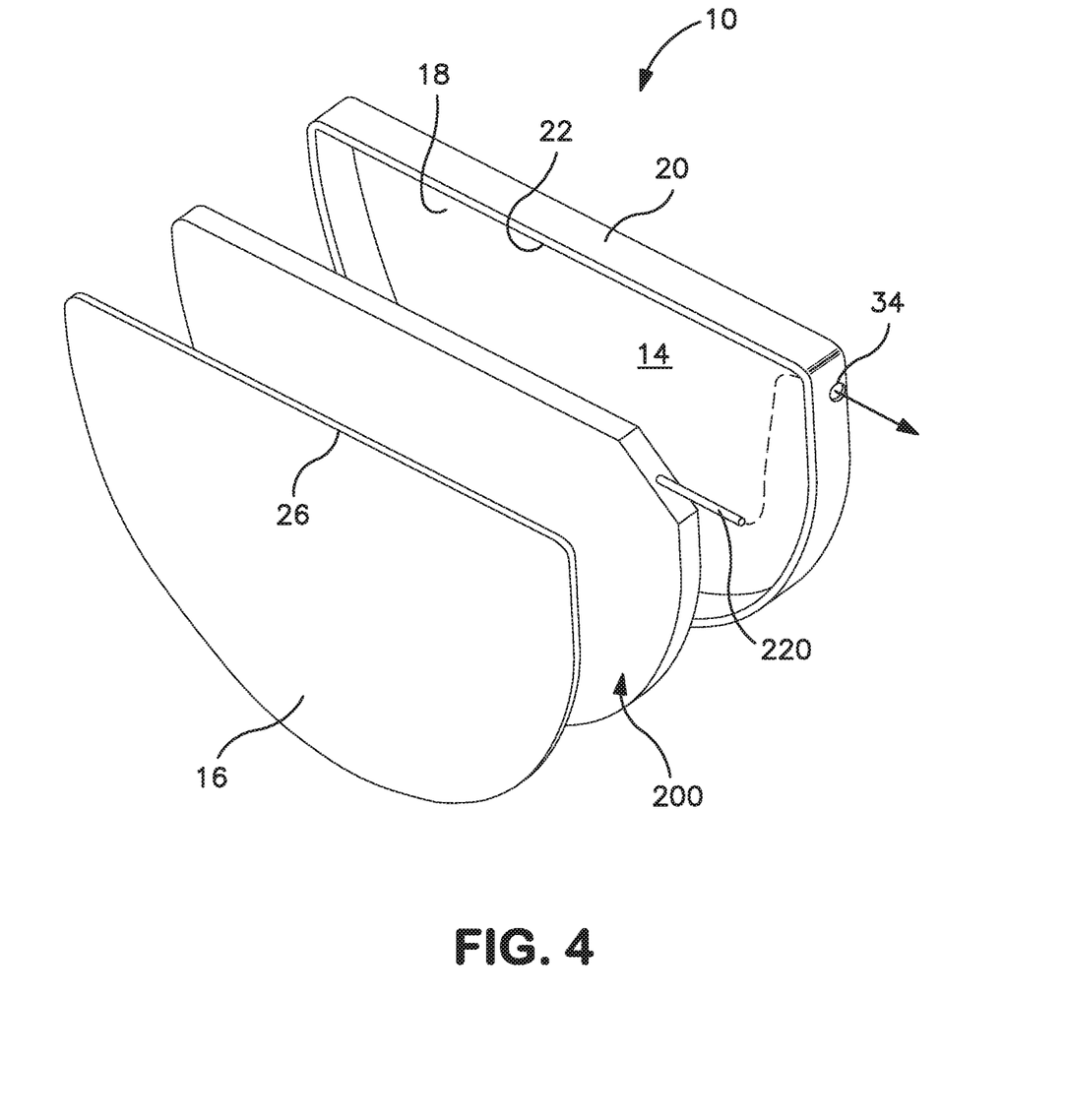
FIG. 4 is a perspective view illustrating the assembly of the anode of FIG. 2 with casing components to form the capacitor shown in FIG. 1.

The particular manner in which the components are incorporated into the capacitor is not critical and may be accomplished using a variety of techniques. In most embodiments, however, the anode is positioned within a casing. Referring to FIGS. 1 and 4, for example, one embodiment of a capacitor 10 is shown that includes the anode 200 shown in FIGS. 2-3. Although only one anode is shown, it should be understood that multiple anodes (e.g., stack) may be employed as is described, for instance, in U.S. Pat. No. 7,483,260 to Ziarniak, et al. In the illustrated embodiment, the anode 200 may be positioned within a casing 12 made of a first casing member 14 and a second casing member 16. The first casing member 14 has a face wall 18 joined to a surrounding sidewall 20, which extends to an edge 22. The second casing member 16 may likewise contain a second face wall 24 having a surrounding edge 26. In the illustrate embodiment, the second casing member 16 is thus in the form of a plate that serves as a lid for the casing 10. The casing members 14 and 16 may be hermetically sealed together by welding (e.g., laser welding) the edges 22 and 26 where they contact each other. The casing members 14 and/or 16 may be analogous to the metal substrate described above such that a conductive polymer coating (not shown) may be deposited on the interior surface thereof. Alternatively, a separate metal substrate may be located adjacent to the casing member 14 and/or 16 and applied with the conductive polymer coating.

Although not shown, one or more separators may be employed between the anode and cathode (e.g., between the anode 200 and the first casing member 14, between the anode 200 and the second casing member 16, or between the anode and both casing members) that help insulate the anode and conductive polymer-coated cathode from each other. Examples of suitable materials for this purpose include, for instance, porous polymer materials (e.g., polypropylene, polyethylene, etc.), porous inorganic materials (e.g., fiberglass mats, porous glass paper, etc.), ion exchange resin materials, etc. Particular examples include ionic perfluorinated sulfonic acid polymer membranes (e.g., Nafion™ from the E.I. DuPont de Nemeours & Co.), sulphonated fluorocarbon polymer membranes, polybenzimidazole (PBI) membranes, and polyether ether ketone (PEEK) membranes. Although preventing direct contact between the anode and cathode, the separator permits ionic current flow of the electrolyte to the electrodes.

A feedthrough 30 (FIG. 1) may also be employed that electrically insulates the anode wire 200 from the casing 12. The feedthrough 30 extends from within the casing 12 to the outside thereof. A hole 34 may be provided in the surrounding sidewall 20 of the casing member 14 into which the feedthrough 30. The feedthrough 30 may, for example, be a glass-to-metal seal ("GTMS") that contains a ferrule (not shown) with an internal cylindrical bore of a constant inside diameter. An insulative glass can thus provide a hermetic seal between the bore and the anode wire 200 passing therethrough. After assembly and sealing (e.g., welding), the electrolyte may optionally be introduced into the casing through a fill-port. Filling may be accomplished by placing the capacitor in a vacuum chamber so that the fill-port extends into a reservoir of the electrolyte. When the chamber is evacuated, pressure is reduced inside the capacitor. When the vacuum is released, pressure inside the capacitor re-equilibrates, and the electrolyte is drawn through the fill-port into the capacitor.

Regardless of its particular configuration, the capacitor of the present invention may exhibit excellent electrical properties. For example, the capacitor may exhibit a high volumetric efficiency, such as from about 50,000 µF*V/cm$^3$ to about 300,000 µF*V/cm$^3$, in some embodiments from about 60,000 µF*V/cm$^3$ to about 200,000 µF*V/cm$^3$, and in some embodiments, from about 80,000 µF*V/cm$^3$ to about 150,000 µF*V/cm$^3$, determined at a frequency of 120 Hz and at room temperature (e.g., 25° C.). Volumetric efficiency is determined by multiplying the formation voltage of a part by its capacitance, and then dividing by the product by the volume of the part. For example, a formation voltage may be 175 volts for a part having a capacitance of 520 µF, which results in a product of 91,000 µF*V. If the part occupies a volume of about 0.8 cm$^3$, this results in a volumetric efficiency of about 113,750 µF*V/cm$^3$.

The capacitor may also exhibit a high energy density that enables it suitable for use in high pulse applications. Energy density is generally determined according to the equation $E=\frac{1}{2}CV^2$, where C is the capacitance in farads (F) and V is the working voltage of capacitor in volts (V). The capacitance may, for instance, be measured using a capacitance meter (e.g., Keithley 3330 Precision LCZ meter with Kelvin Leads, 2 volts bias and 1 volt signal) at operating frequencies of from 10 to 120 Hz (e.g., 120 Hz) and a temperature of 25° C. For example, the capacitor may exhibit an energy density of about 2.0 joules per cubic centimeter (J/cm$^3$) or more, in some embodiments about 3.0 J/cm$^3$, in some embodiments from about 3.5 J/cm$^3$ to about 10.0 J/cm$^3$, and in some embodiments, from about 4.0 to about 8.0 J/cm$^3$. The capacitance may likewise be about 1 milliFarad per square centimeter ("mF/cm$^2$") or more, in some embodiments about 2 mF/cm$^2$ or more, in some embodiments from about 5 to about 50 mF/cm$^2$, and in some embodiments, from about 8 to about 20 mF/cm$^2$. The capacitor may also exhibit a relatively high "breakdown voltage" (voltage at which the capacitor fails), such as about 180 volts or more, in some embodiments about 200 volts or more, and in some embodiments, from about 210 volts to about 260 volts.

The equivalent series resistance ("ESR")—the extent that the capacitor acts like a resistor when charging and discharging in an electronic circuit—may also be less than about 15,000 milliohms, in some embodiments less than about 10,000 milliohms, in some embodiments less than about 5,000 milliohms, and in some embodiments, from about 1 to about 4,500 milliohms, measured with a 2-volt bias and 1-volt signal at a frequency of 120 Hz. In addition, the leakage current, which generally refers to the current flowing from one conductor to an adjacent conductor through an insulator, can be maintained at relatively low levels. For example, the numerical value of the normalized leakage current of a capacitor of the present invention is, in some embodiments, less than about 1 pA/µF*V, in some embodiments less than about 0.5 pA/µF*V, and in some embodiments, less than about 0.1 pA/µF*V, where pA is microamps and µF*V is the product of the capacitance and the rated voltage. Leakage current may be measured using a leakage test meter (e.g., MC 190 Leakage test, Mantracourt Electronics LTD, UK) at a temperature of 25° C. and at a certain rated voltage after a charging time of from about 60 to about 300 seconds. Such ESR and normalized leakage current values may even be maintained after aging for a substantial amount of time at high temperatures. For example, the values may be maintained for about 100 hours or more, in some embodiments from about 300 hours to about 2500 hours, and in some embodiments, from about 400 hours to about 1500 hours (e.g., 500 hours, 600 hours, 700 hours, 800 hours, 900 hours, 1000 hours, 1100 hours, or 1200 hours) at temperatures ranging from about 100° C. to about 250° C., and, in some embodiments from about 100° C. to about 200° C. (e.g., 100° C., 125° C., 150° C., 175° C., or 200° C.).

The electrolytic capacitor of the present invention may be used in various applications, including but not limited to implantable medical devices, such as implantable defibrillators, pacemakers, cardioverters, neural stimulators, drug administering devices, etc. In one embodiment, for example, the capacitor may be employed in an implantable medical device configured to provide a therapeutic high voltage (e.g., between approximately 500 volts and approximately 850 volts, or, desirably, between approximately 600 Volts and approximately 900 volts) treatment for a patient. The device may contain a container or housing that is hermetically sealed and biologically inert. One or more leads are electrically coupled between the device and the patient's heart via a vein. Cardiac electrodes are provided to sense cardiac activity and/or provide a voltage to the heart. At least a portion of the leads (e.g., an end portion of the leads) may be provided adjacent or in contact with one or more of a ventricle and an atrium of the heart. The device may also contain a capacitor bank that typically contains two or more capacitors connected in series and coupled to a battery that is internal or external to the device and supplies energy to the capacitor bank. Due in part to high conductivity, the capacitor of the present invention can achieve excellent electrical properties and thus be suitable for use in the capacitor bank of the implantable medical device.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A wet electrolytic capacitor comprising:
   an anode that comprises a pellet formed from a pressed and sintered tantalum powder, the tantalum powder comprising primary particles having a median size (D50) of about 5 nm to about 250 nm, wherein a tantalum pentoxide dielectric layer is formed on the pellet that has no more than about 1,000 crystals per square millimeter or less;
   a cathode that comprises a metal substrate coated with a conductive coating; and
   a fluidic working electrolyte in communication with the anode and the cathode.

2. The capacitor of claim 1, wherein the anode has a thickness of about 5 millimeters or less.

3. The capacitor of claim 1, wherein a leadwire extends from the anode.

4. The capacitor of claim 1, wherein the anode has a D-shape.

5. The capacitor of claim 1, wherein the metal substrate includes titanium or stainless steel.

6. The capacitor of claim 1, wherein the conductive coating includes a substituted polythiophene.

7. The capacitor of claim 1, wherein the electrolyte has a pH of from about 5.0 to about 7.5.

8. The capacitor of claim 1, wherein a separator is positioned between the anode and cathode.

9. The capacitor of claim 1, wherein the capacitor contains a casing that contains a first casing member and a second casing member between which the anode and the fluid working electrolyte are disposed, wherein the metal substrate forms at least a portion of the first casing member, the second casing member, or both.

10. The capacitor of claim 9, wherein the first casing member contains a face wall and a surrounding sidewall that extends to an edge, and further wherein the second casing member is in the form of a lid that is sealed to the edge of the sidewall.

11. An implantable medical device comprising the capacitor of claim 1.

12. A method for forming a wet electrolytic capacitor, the method comprising forming an anode that comprises a pellet formed from a pressed and sintered tantalum powder, the tantalum powder comprising primary particles having a median size (D50) of about 5 nm to 250 nm, wherein a tantalum pentoxide dielectric layer is formed on the pellet that has no more than about 1,000 crystals per square millimeter or less by subjecting the sintered anode pellet to a formation profile, wherein the formation profile includes subjecting the pellet to an increasing current so that a target forming voltage is achieved in about 30 minutes or less, and positioning the anode and a fluidic working electrolyte within a casing,
   wherein the wet electrolytic capacitor further comprises a cathode that comprises a metal substrate coated with a conductive coating; and a fluidic working electrolyte in communication with the anode and the cathode.

13. The method of claim 12, wherein the current is increased to a peak current, which is reached in about 30 minutes or less.

14. The method of claim 13, wherein the peak current ranges from about 1,000 to about 6,000 milliamps.

15. The method of claim 12, wherein the target forming voltage ranges from about 100 to about 500 volts.

16. The method of claim 12, wherein the formation profile further includes decreasing the current after the formation voltage is achieved.

17. The method of claim 16, wherein the current is decreased at a non-linear rate.

18. The method of claim 16, wherein the target forming voltage is held at a relatively constant level as the current is decreased.

19. The method of claim 18, wherein the target forming voltage is held relatively constant for a period of time ranging from about 20 minutes to about 300 minutes.

* * * * *